United States Patent [19]

De Vincentiis

[11] Patent Number: 4,634,701
[45] Date of Patent: Jan. 6, 1987

[54] FURAN DERIVATIVES HAVING ANTI-ULCER ACTIVITY

[75] Inventor: Leonardo De Vincentiis, Rome, Italy

[73] Assignee: Ausonia Farmaceutici s.r.l., Rome, Italy

[21] Appl. No.: 738,668

[22] Filed: May 28, 1985

[30] Foreign Application Priority Data

Jun. 6, 1984 [IT] Italy ............................ 21273 A/84

[51] Int. Cl.$^4$ .................... A61K 31/34; C07D 307/52; C07D 307/54
[52] U.S. Cl. .................... 514/232; 548/336; 514/248; 548/467; 548/517; 514/252; 549/58; 549/365; 514/305; 549/366; 549/435; 514/307; 549/461; 549/467; 514/309; 549/471; 549/495; 514/312; 514/314; 514/326; 514/367; 514/375; 514/394; 514/414; 514/422; 514/443; 514/452; 514/465; 514/466; 514/469; 514/470; 514/471; 544/152; 544/238; 544/379; 546/121; 546/145; 546/148; 546/157; 546/214; 548/178; 548/179; 548/217; 548/221
[58] Field of Search .................... 544/152, 238, 379; 546/121, 145, 148, 157, 214; 548/178, 179, 217, 221, 336, 467, 517; 549/58, 461, 471, 365, 495, 366, 435, 467; 514/232, 248, 252, 305, 307, 309, 312, 314, 326, 367, 375, 394, 414, 422, 443, 452, 465, 466, 469, 470, 471

[56] References Cited

U.S. PATENT DOCUMENTS 4,233,302 11/1980 Martin-Smith et al. ........ 549/495 X
4,252,819 2/1981 Horata et al. .................. 549/495 X
4,279,819 7/1981 Price et al. ..................... 549/495 X
4,427,685 1/1984 Stemp ............................ 549/495 X
4,492,711 1/1985 Nisato et al. .................... 549/495 X

OTHER PUBLICATIONS

Moroni, Chemical Abstracts, vol. 100 (1984) 103160q.

Primary Examiner—Richard L. Raymond
Attorney, Agent, or Firm—Bruce M. Collins

[57] ABSTRACT

Compounds of formula (I):

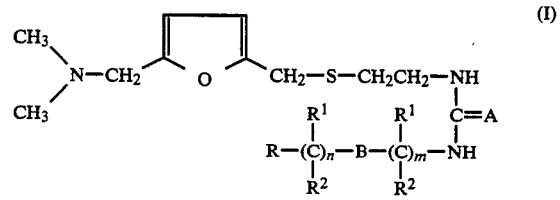

wherein:

A represents a $CH-NO_2$ group or a N-CN group;
B represents $CH_2$, O, S or a direct bond;
R represents a bicyclic or polycyclic residue, variously substituted and functionalized;
$R^1$ and $R^2$, which may be the same or different, are hydrogen or $C_1-C_4$ alkyl groups; and
n and m, which may be the same or different, are 0, 1, 2, 3 or 4;

are valuable pharmacological agents.

25 Claims, No Drawings

FURAN DERIVATIVES HAVING ANTI-ULCER ACTIVITY

The present invention relates to furan compounds having antiulcer activity, due to their action on $H_1$ and $H_2$ histamine receptors, according to Ash and Schild (Brit. J. Pharmacol. Chemoth. 27, 427-1966).

More particularly, the present invention relates to compounds of formula (I):

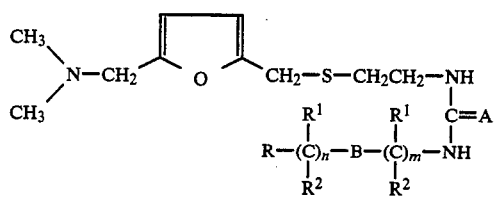

wherein:
- A represents a $CH-NO_2$ group or a $N-CH$ group;
- B represents a $CH_2$ group, an oxygen or sulfur atom, or a single bond;
- R represents a bicyclic or polycyclic residue, which may be either completely aromatic or partially or entirely hydrogenated, said residue optionally containing one or more nitrogen, oxygen or sulfur atoms in place of carbon atoms and one or more substituents, which may be:
    - $C_1$-$C_4$ alkyl groups, $C_2$-$C_4$ alkenyl or alkinyl groups, having straight or branched chain, said chain being optionally interrupted by oxygen, nitrogen or sulfur atoms, and containing such substituents as OH, SH, $NH_2$, $NO_2$ groups or halogen atoms;
    - $C_1$-$C_4$ amino, monoamino or dialkylamino groups; pyrrolidino, piperidino, piperazino or morpholino groups; $C_1$-$C_4$ alkoxy or alkylmercapto groups; CN, $NO_2$, COOH groups; halogen atoms;
    - phenyl groups having one or more $R^3OCH_2CH_2O-$ groups, in which $R^3$ is a $C_1$-$C_4$ linear or branched alkyl group;
- $R^1$ and $R^2$ which may be the same or different, represent hydrogen or $C_1$-$C_4$ alkyl groups;
- n and m, which may be the same or different, are 0, 1, 2, 3 or 4;

with the proviso that when B is $CH_2$ and A is $CH-NO_2$, m and n are 0 and R represents a residue different from 3,4-methylenedioxyphenyl.

The present invention also relates to pharmaceutically acceptable acid addition salts of compounds (I) and to possible hydrated forms of said compounds (I) and salts thereof.

More particularly, in the above formula (I) R may represent:

(a) a naphthyl residue of formula Ia

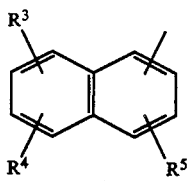

wherein $R^3$, $R^4$ and $R^5$, which may be the same or different, are hydrogen, halogen, $NO_2$, OH, $C_1$-$C_4$ linear or branched alkyl groups, $C_2$-$C_4$ linear or branched alkenyl or alkinyl groups, $C_1$-$C_4$ alkoxy or alkylmercapto groups, said alkyl or alkenyl chains being possibly interrupted by oxygen, sulfur or nitrogen atoms, and being possibly substituted with nitro, amino, hydroxy or mercapto groups or halogen atoms; $C_1$-$C_4$ amino, mono- or dialkylamino groups, pyrrolidino, piperidino, piperazino or morpholino groups; the residue of formula (Ia) being optionally or totally hydrogenated;

(b) a bicyclic residue containing one or more heteroatoms, having formula (Ib)

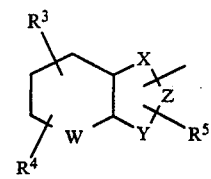

where W, X, Y and Z may independently represent oxygen or sulfur atoms, or $CH_2$ or NH groups, X, Y or Z representing optionally a $-CH_2-CH_2-$ group, and where $R^3$, $R^4$ and $R^5$ have independently the above mentioned meanings, the residue of formula (Ib) being optionally partially or totally dehydrogenated;

(c) a residue of formula (Ic)

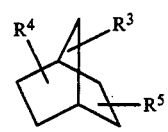

wherein $R^3$, $R^4$ and $R^5$ have independently the above mentioned meanings, and residue (Ic) may also be partially dehydrogenated;

(d) a residue of formula (Id)

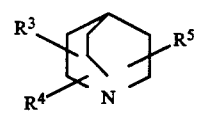

wherein $R^3$, $R^4$ and $R^5$ have independently the above mentioned meanings;

(e) a residue of formula (Ie)

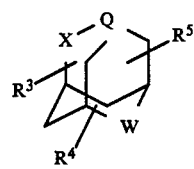

wherein $R^4$, X and W and $R^3$, $R^4$ and $R^5$ independently have the above mentioned meanings, and Q represents a nitrogen atom or a CH group.

The following is a list of representative non-limiting examples of compounds (I) of the present invention.

N-[2-[[[5-(dimethylamino)methyl-2-furanyl]methyl]-thio]ethyl]-N'-[4-[2-(methoxy)ethoxy]benzyl]-2-nitro-1,1-ethenediamine;

N-cyano-N'-[2-[[[5-(dimethylamino)methyl-2-furanyl]-methyl]thio]ethyl]-N''-[2-[2-(methoxy)ethoxy]-benzyl]guanidine;

N-[2-[[[5-(dimethylamino)methyl-2-furanyl]methyl]-thio]ethyl]-N'-[[[4-[2-(methoxy)ethoxy]benzyl]-thio]propyl]-2-nitro-1,1-ethenediamine;

N-[2-[[[5-(dimethylamino)methyl-2-furanyl]methyl]-thio]ethyl]-N'-[2-[[7-(methoxy-4-methylthio)cumaryl]-ethyl]-2-nitro-1,1-ethenediamine;

N-[2-[[[5-(dimethylamino)methyl-2-furanyl]methyl]-thio]ethyl]-N'-[2-[2-(methylthioethyl)benzo-1,4-dioxan]-2-nitro-1,1-ethenediamine;

N-[2-[[[5-(dimethylamino)methyl-2-furanyl]methyl]-thio]ethyl]-N'-[3-(1-methoxy-indanyl-2-oxy)propyl]-2-nitro-1,1-ethenediamine;

N-[2-[[[5-(dimethylamino)methyl-2-furanyl]methyl]-thio]ethyl]-N'-[2-[[2-[2,3-dihydrobenzofuranyl]methyl]-thio]ethyl]-2-nitro-1,1-ethenediamine;

N-cyano-N'-[2-[[[5-(dimethylamino)methyl-2-furanyl]-methyl]thio]ethyl]-N''-[2-(5-methylbenzofuranyl)-ethyl]guanidine;

N-[2-[[[5-(dimethylamino)methyl-2-furanyl]methyl]-thio]ethyl]-N'-[2-(1,4-benzodioxane-7-methylthio]-ethyl]-2-nitro-1,1-ethenediamine;

N-cyano-N'-[2-[[[5-(dimethylamino)methyl-2-furanyl]-methyl]thio]ethyl]-N''-[2-(1,4-benzodioxan-7-methyloxy]ethyl]guanidine;

N-[2-[[[5-(dimethylamino)methyl-2-furanyl]methyl]-thio]ethyl]-N'-[3-[2-(1,4-benzodioxan)]propyl]-2-nitro-1,1-ethenediamine;

N-cyano-N'-[2-[[[5-(dimethylamino)methyl-2-furanyl]-methyl]thio]ethyl]-N''-[2-(1,3-benzodioxan)-6-chloro-8-methylthio)ethyl]guanidine;

N-[2-[[[5-(dimethylamino)methyl-2-furanyl]methyl]-thio]ethyl]-N'-[2-(2,3-dihydrobenzofuranyl-2-methyl-5-methyloxy)]ethyl]-2-nitro-1,1-ethenediamine;

N-[2-[[[5-dimethylamino)methyl-2-furanyl]methyl]-thio]ethyl]-N'-[2-[3-(thionaphtenyl)methyleneoxy]-ethyl]-2-nitro-1,1-ethenediamine;

N-[2-[[[5-(dimethylamino)methyl-2-furanyl]methyl]-thio]ethyl]-N'-[2-[(6-methylcumarinyl)methyloxy]-ethyl]-2-nitro-1,1-ethenediamine;

N-[2-[[[5-(dimethylamino)methyl-2-furanyl]methyl]-thio]ethyl]-N'-[3-[(6-ethoxybenzothiazolyl)-2-thio]-propyl]-2-nitro-1,1-ethenediamine.

Compounds of formula (I) according to the invention, form pharmaceutically acceptable salts, with both inorganic and organic acids. Particularly preferred are: hydrochloric, hydrobromic, sulphate and phosphate salts; acetate, benzoate, butyrate, fumarate, maleate, tartrate, p-toluensulphonate, methansulphonate, naphthalenesulphonate, glutamate, aspartate salts.

Compounds I may be administered by oral, parenteral, rectal or topic route, in form of capsules, tablets, pillules, syrups, vials, suppositories, creams, gels, ointments, in free or salified form, together suited with diluents, vehicles or excipients. Compounds I may also be used in slow release phormulations.

Compounds (I) may be prepared according to our italian patent appln. n. 19929 A/84, filed on Mar. 7, 1984 which discloses a process for preparing N-[2-[[[5-[(dimethylamino)methyl]-2-furanyl]methyl]-thio]ethyl-N'-(3,4-methylendioxybenzyl)-2-nitro-1,1-ethenediamine. Said process is summarized as follows:

SCHEME I

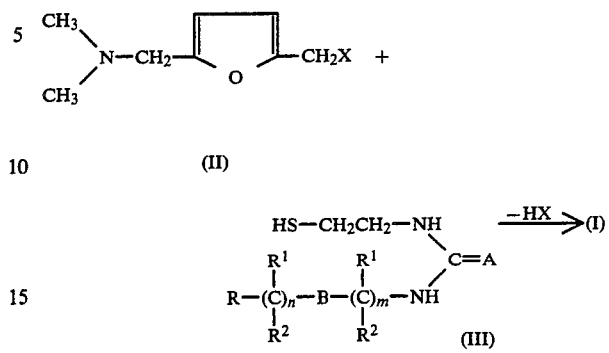

(II)

wherein A, B, R, $R^1$, $R^2$, m and n have the above mentioned meanings, and X represents a leaving group, such as a OH, $N(CH_3)_2$ or $N^+(CH_3)_3$ group or an halogen atom.

Intermediates (III) may be obtained by reacting a 2,2-bis-(methylthio)methylene derivative (IV) with an amine of general formula (V), according to the following scheme:

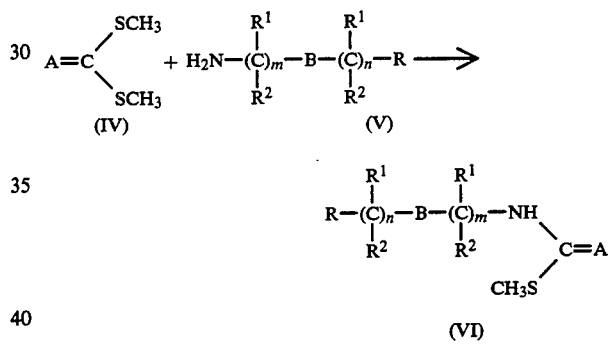

The resulting compounds (VI) are treated first with ammonia, then with ethylene sulfide, to give compounds (III):

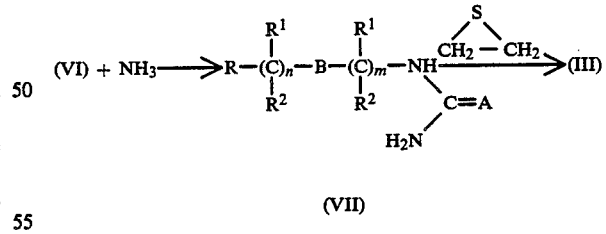

or they may be obtained by treating (IV) with ammonia, and the resulting intermediates (VIII) with ethylene sulfide, to give compounds (IX) which are treated with amines (V) to yield intermediates (III):

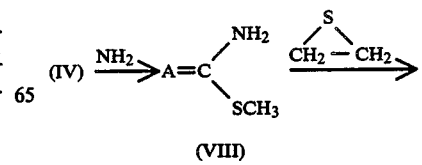

(VIII)

-continued

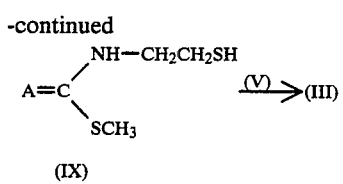

(IX)

or by treating a thiazolidine (X) with an amine (V), according to the following scheme:

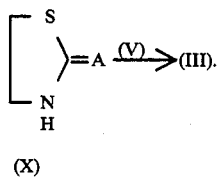

In the above schemes A, B, R, $R^1$, $R^2$, m and n having the above mentioned meanings.

SCHEME II (II) + HS—CH$_2$CH$_2$NH

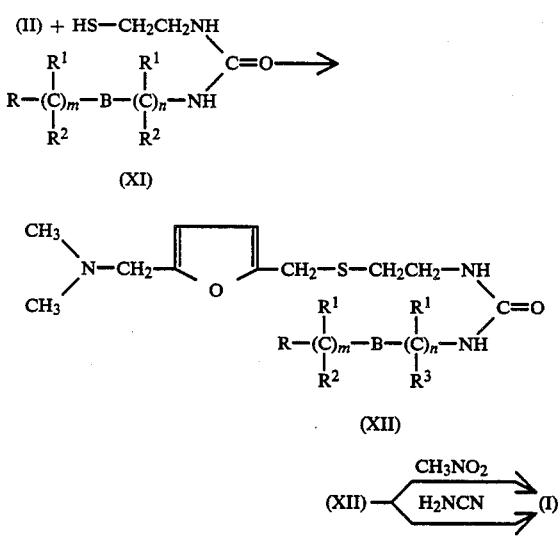

Ureas (XI) may be obtained by reacting an amine (V) with a N,N'-carbonyl-diimidazole, to give imidazole-carbonylamides (XIII) which are directly reacted with cysteamine, according to the following scheme:

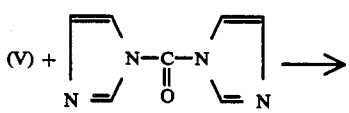

-continued

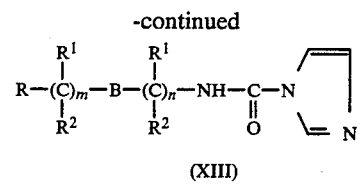

(XIII)

(XIII) + H$_2$N—CH$_2$CH$_2$SH ⟶ (XI).

Alternatively, cysteamine may be substituted by 2,2'-diaminodiethyldisulfide, which is reacted with intermediate (XIII) in 1:2 ratio. The resulting disulfide is then reduced with zinc and acetic acid, to give 2 molecules of (XI).

A, B, R, $R^1$, $R^2$, m and n have the above mentioned meanings.

SCHEME III

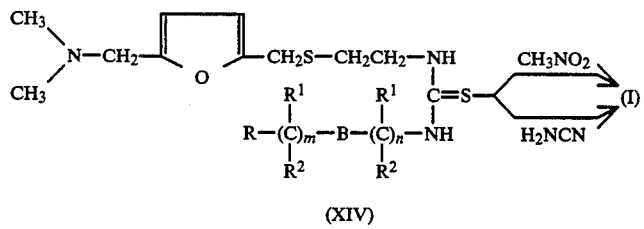

(XIV)

Thioureas (XIV) may be obtained by reacting isothiocyanates (XV) with cysteamine and subsequently treating the resulting intermediates (XVI) with furan derivatives (II):

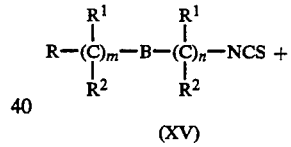

(XV)

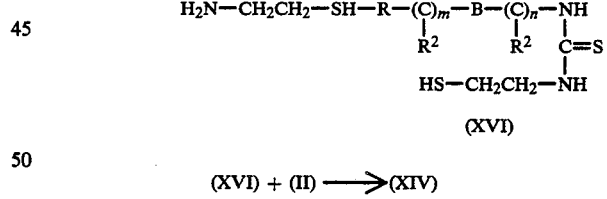

(XVI)

(XVI) + (II) ⟶ (XIV)

wherein A, B, R, $R^1$, $R^2$, m and n have the above mentioned meanings.

SCHEME IV

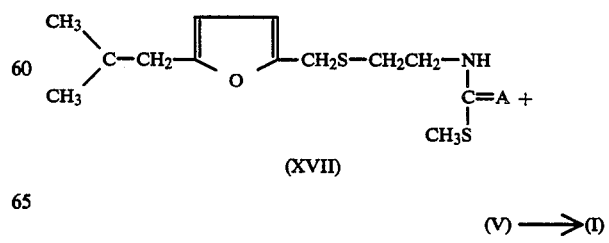

(XVII)

(V) ⟶ (I)

(wherein A has the above mentioned meanings).

SCHEME V

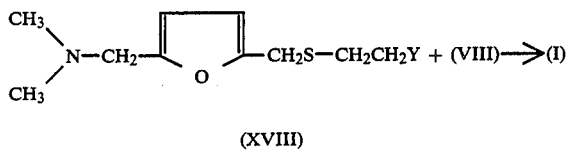

(XVIII)

wherein Y represents a hydroxy or tosyloxy group, in the first instance the reaction being carried on in the presence of Nickel Raney.

The following examples illustrate the present invention without limit the scope thereof.

EXAMPLE 1

N-[2-[[[5-(Dimethylamino)methyl-2-furanyl]methyl]-thio]ethyl]-N'-[4-[2-(methoxy)ethoxy]benzyl]-2-nitro-1,1-ethendiamine (a) 4-(Chloroethoxy)benzyl chloride 10 Grams (0.06 mol) of 4-(2-hydroxyethoxy)benzyl alcohol, prepared according to L. M. Marson, Il Farmaco ed. sci. 14, 159 (1959)), was dissolved in anhydrous pyridine (80 ml) and anhydrous chloroform (100 ml), then the mixture was ice cooled and thionyl chloride (80 ml) was slowly added, under stirring. Stirring was continued, allowing temperature to raise to the room's one, then the mixture was heated for about 2 hours to complete the reaction. After cooling, the reaction mixture was poured into water (200 ml); the chloroformic layer was separated, washed with a 5% aqueous solution of sodium hydroxyde, dried over $Na_2SO_4$ and evaporated. The residue was distilled under vacuum to provide the pure product (8.2 g; 66.6% yield).

Chlorine (Schoeniger): calc. 34.57% found 34.77%.

(b) 4-(2-Chloroethoxy)benzylamine

To a mixture of 20% aqueous ammonia (20 ml; 0,24 mol) and ether (20 ml), cooled to $-15°$ C., 4-(2-chloroethoxy)benzyl chloride (5.0 g; 0.024 moles) was dropped during about 30 minutes. The reaction mixture was warmed to room temperature and filtered, the etheric layer was separated, washed with water and extracted with diluted hydrochloric acid. The combined acidic layers were treated with 25% NaOH, then extracted again with ether.

The etheric layer was dried ($K_2CO_3$) and evaporated to give an oily residue containing the desired compound and bis[4-(2-chloroethoxy)benzyl]imine, which was chromatographed on a silica gel column, eluting with diethyl ether-petroleum ether (1:2) to provide the pure product (2.2 g; 49.3%) in form of a yellow oil.

Nitrogen (Kjeldahl): calc. 7.5% found 7.7%.

(c) 4-(2-(Methoxy)ethoxy)benzylamine 4-(2-Chloroethoxy)benzylamine (2.0 g; 0,11 mol) was dissolved in anhydrous toluene (50 ml). The reaction mixture was ice-cooled and sodium methoxide (0.59 g; 0.011 mol) dissolved in methanol (5 ml) was added thereto. When the addition was complete the mixture was left to stand for 2 hours at room temperature and filtered. Solvent was evaporated from the filtrate, to give an oily residue of good purity.

Nitrogen (Kjeldahl): calc. 7.89% found 7.72%.

(d) 1-Nitro-2-[4-[2-(methoxy)ethoxy]benzylamino]-2-]2-(mercaptoethyl)amino]ethene 2-(Nitromethylene)thiazolidine (14.6 g; 0.1 mol) (French Patent No. 2,384,765) was dissolved in benzene, heating to slight reflux, and 4-[2-(methoxy)ethoxy]benzylamine (35.4 g; 0.2 mol) was added during 60 minutes. The reaction mixture was heated again for some hours, then it was cooled and filtered; the filtrate was washed in turn with water, diluted HCl, 5% aqueous NaOH, water, and dried over $Na_2SO_4$. Solvent was evaporated under reduce pressure to afford a residue which was purified by means of chromatography on a silica gel column (70-230 mesh) eluted with ethyl acetate/petroleum ether. The analytically pure product was obtained (21.9 g; 67% yield).

Sulfur (Shoeniger): calc. 9.79%; found 9.66%.

(e) 2-(Dimethylaminomethyl)-5-chloromethylfuran 2-(Dimethylaminomethyl)-5-hydroxymethylfuran (15.6 g; 0.1 mol), prepared according to E. W. Gill et al. (J. Chem. Soc. 1958, 4728) dissolved dichloromethane (100 ml) was trated first with gaseous HCl, then with $PCl_5$ at room temperature in heterogeneous phase, to give the title compound (14.0 g; 80.6% yield).

Chlorine (Schoeniger)-calc. 20.42%; found 20.60%.

(f) Title compound

1-Nitro-2-[4-[2-(methoxy)-ethoxy]benzylamino]-2-[2-(mercaptoethyl)amino]ethene (16.4 g; 0.05 mol) was added to a solution of 1.15 g (0.05 g-atom) of sodium in 100 ml of anhydrous ethanol. The reaction mixture was refluxed for 20 minutes, then cooled and slowly added with 2-(dimethylaminomethyl)-5-chloromethyl-furan (9.1 g; 0.05 mol) in absolute ethanol (50 ml), under stirring. The mixture was heated to 50°-80° C. for about 2 hours, added with water till turbidity, left to stand overnight, to give a crystalline precipitate (17.8 g; 77% yield) upon filtration.

Elemental analysis: for $C_{22}H_{32}N_4O_5S$ (464.58); calc.% C=56.87; H=6.94; N=12.06; S=6.90; found % C=56.97; H=7.00; N=12.12; S=6.82.

EXAMPLE 2

N-Cyano-N'-[2-[[[5-(dimethylamino)methyl-2-furanyl]methyl]thio]ethyl]-N''-[2-[2-(methoxy)ethoxy]benzyl]-guanidine (a) 2-[2-(Methoxy)ethoxy]benzylamine This intermediate was prepared as described in Example 1 for the "para" isomer (69% yield).

Nitrogen (Kjeldahl): calc. 7.7%; found 7.6%.

(b) 2-[[[5-(Dimethylamino)methyl-2-furanyl]methyl]thio]-ethylamine

Cysteamine hydrochloride (5.7 g; 0.05 mol) was dissolved in conc. hydrochloric acid (20 ml). Upon ice-cooling, 5-(dimethylamino)methyl-2-furanemethanol (7.75 g; 0.05 mol) was added. The reaction mixture was left to stand at 0° C. for 20 hours, added with a $Na_2CO_3$ excess, extracted with ether and filtered. The filtrate was evaporated to obtain an oily residue which after distillation in vacuo (p.e. 105°-107°; 0.1 mm) gave the pure product (6.0 g; 56% yield).

(c)
N-Cyano-N'-[2-[[[5-(dimethylamino)methyl-2-furanyl]-methyl]-thio]ethyl]-S-(methyl)isothiourea Dimethyldithiocyanoiminocarbonate (7.3 g; 0.05 mol) was dissolved in 1,1,2-trichloroethylene (100 ml). The mixture was heated till homogeneity. The ethylamine derivative described in step (b) (5.3 g; 0.025 mol) dissolved in the same solvent (50 ml) was added to the boiling solution. Boiling was continued for about 90 minutes, then the solvent was removed under reduced pressure and the residue was chromatographed on silica gel, eluting first with petroleum ether, then with dichloromethane. 5.2 Grams (67% yield) of pure product were obtained.

Sulfur (Schoeniger): calc. 20.5%; found 20.8%.

(d) Title compound

2-[2-(Methoxy)ethoxy]benzylamine (2.9 g; 0.016 mol) and isothiourea (5 g; 0.016 mol) previously prepared respectively in step (a) and (c) were reacted in benzene. The crude product was purified by chromathography on silica gel, eluting with methanol. The product was recrystallized from ethanol/ether, to give 3.4 g (48% yield).

Elemental analysis: for $C_{22}H_{31}N_5O_3S$ (445.59); calc.% C=59.30; H=7.01; N=15.72; S=7.19; found % C=59.15; H=6.99; N=15.80; S=7.22.

EXAMPLE 3

N-[2-[[[5-(Dimethylamino)methyl-2-furanyl]methyl]-thio]ethyl]-N'-[[[4-(2-methoxyethoxy)benzyl]thio]-propyl]-2-nitro-1,1-ethenediamine (a) 4-(2-Methoxyethoxy)benzyl chloride 4-Hydroxybenzyl alcohol (24.9 g; 0.2 mol) was dissolved in ethanol (200 ml). NaOH (8.0 g; 0.2 mol) dissolved in water (10 ml) was added to the solution. After boiling for about 30 minutes, 2-methoxyethylebromide (27.8 g; 0.2 mol) was added dropwise in about 90 minutes. The reaction mixture was cooled and filtered. The filtrate was evaporated, to give a residue which was chromatographed on silica gel column, eluted with methanol/ether (1:3).

The resulting product (90.2; 83% yield) was directly treated with thionyl chloride in anhydrous pyridine, according to the procedure described in Example 1a), obtaining a 65% yield.

Chloro (Schoeniger): calc. 17.6%; found 17.8%.

(b) 4-(2-Methoxyethoxy)benzylmercaptan

The previously obtained intermediate (18.2 g; 0.1 mol) was dissolved in isopropanol and treated with $NaSH.H_2O$ (7.4 g; 0.1 mol) under cooling. After completion of the addition, the reaction mixture was progressively heated to 50°–80° C. for about 3 hours. After cooling and filtration, the solvent was removed under reduced pressure, to give an oily residue (15.6 g; 79% yield) which was directly used for the next step.

(c) 3-[[4-(2-Methoxyethoxy)benzyl]thio]propylamine 4-(2-Methoxyethoxy)benzylmercaptane (10 g; 0.02 mol) was dissolved in absolute ethanol (100 ml) and treated with metal sodium in fragments (0.92 g; 0.04 g.a.). 3-Chloropropylamine hydrochloride (2.8 g; 0.02 mol) was then added till a temperature below 10° C. The reaction mixture was left to stand overnight, then filtered and the filtrate was evaporated in vacuo. The resulting residue was purified according to W. C. Still et al. (J. Org. Chem. 43, 2923-1978). The analytically pure product (4.3 g; 84% yield) was a slightly yellowish oil.

Sulfur (Schoeniger): calc. 12.5%; found 12.4%.

(d)
N-[[[4-(2-Methoxyethoxy)benzyl]thio]propyl]-N'-(3-mercaptoethyl)-2-nitro-1,1-ethenediamine By reacting the previously prepared amine with 2-(nitromethylene)thiazolidine, according to the procedure described in Example 1d), the desired product was obtained with a 49% yield.

Elemental analysis: for $C_{17}H_{27}N_3O_4S$ (401.54); calc.%: C=50.85; H=6.77; N=13.95; found %: C=60.01; H=6.68; N=13.88.

(e) Title compound

The procedure of Example 1 was repeated, to obtain the title product in a 62% yield.

Elemental analysis: for $C_{25}H_{38}N_4O_5S$ (538.73) calc.%: C=55.73; H=7.11; N=10.40; S=11.90; found %: C=55.57; H=7.01; N=10.36; S=11.53.

EXAMPLE 4

N-[2-[[[5-(Dimethylamino)methyl]-2-furanyl]methyl]-thio]ethyl]-N'-2-[[(7-methoxy-4-methylthio)cumaryl]-ethyl]-2-nitro-1,1-ethenediamine (a) 2-[(7-Methoxy-4-methylthio)cumaryl]ethylamine Cysteamine (7.7 g; 0.1 mol) was dissolved in methanol. NaOH (4 g; 0.1 mol) dissolved in water (5 ml) was added to the solution. After cooling to 0° C., 4-bromomethyl-7-methoxy-cumarin (26.9 g; 0.1 mol) dissolved in ethanol (100 ml) was added. The reaction mixture was heated to mild boiling for 15-30 minutes, thereafter it was left to stand overnight, then filtered. The filtrate was evaporated under reduced pressure, to give a crude product which was purified by silica gel chromatography, eluting with n-propanol/ether.

The pure product (23.8 g; 90% yield) gave the following analytical data:

Sulfur (Schoeniger): calc. 12.08%; found 11.95%.

(b)
1-[[[[5-(Dimethylamino)methyl-2-furanyl]methyl]-thio]ethylamino]-1-methylthio-2-nitro-ethene 2-[[[5-(Dimethylamino)methyl-2-furanyl]methyl]-thio]ethylamine (21.4 g; 0.1 mol) dissolved in trichloroethylene (200 ml) was added to a solution of 1-nitro-2,2-bis(methylthio)ethene (16.5 g; 0.1 mol), during about 30 minutes, under boiling. Boiling was continued for a further 90 minutes, then solvent was evaporated off under reduced pressure and the residue was chromatographed on silica gel, eluting with petroleum ether/dichloromethane. The product was already pure enough for the subsequent step (26.5 g; 79.9% yield).

Sulfur (Schoeniger): calc. 19.34%; found 19.15%.

(c) Title compound

By reacting 2-[(7-methoxy-4-methylthio)cumaryl]ethylamine with nitro-ethene prepared as described in step (b), the title product was obtained in a 67% yield.

Elemental analysis: for $C_{23}H_{32}N_4O_6S_2$ (524.66); calc.%: C=52.65; H=6.15; N=10.67; S=12.22 found %: C=52.54; H=6.05; N=10.77; S=11.98.

EXAMPLE 5

N-Cyano-N'-[2-[[[5-(Dimethylamino)methyl-2-furanyl]-methyl]thio]ethyl]-N''-[2-(2-quinolyl-oxy)ethyl]guanidine

(a) 2-(2-quinolil-oxy)ethylamine

Compound (a) was obtained by reacting 2-chloroquinoline with N-(2-hydroxyethyl)phthalimide; intermediate N-[2-(2-quinolyl-oxy)ethyl]phthalimide was treated with hydrazine in ethanol, to give the desired product in a 31% yield with respect to the starting chloro-quinoline.

Nitrogen: calc. 14.88%; found 15.00%.

(b) N-Cyano-N'-[2-(2-quinoliloxy)ethyl]-S-methyl-isothiourea

The procedure of Example 2 was repeated, to obtain the crude product which was purified according to W. C. Still et al. (J. Org. Chem. 43, 2923-1978). Yield 59%.

Sulfur (Schoeniger): calc. 11.2%; found 11.2%.

(c) Title compound

The procedure described in Example 2 was repeated, to yield the title product.

Elemental analysis: for $C_{23}H_{28}N_6O_2S$ (572.68); calc.%: C=48.24; H=4.93; N=14.67; S=5.60; found %: C=48.42; H=5.10; N=14.50; S=5.70.

EXAMPLE 6

N-[2-[[[5-(Dimethylamino)methyl-2-furanyl]methyl]-thio]ethyl]-N'-[2-(methylthioethyl)benzo-1,4-dioxan]-2-nitro-1,1-ethenediamine

(a) 2-(2-Methylthio-1,4-benzodioxan)ethylamine

To a solution of cysteamine (15.4 g; 0.2 mol) in ethanol (200 ml); NaOH (8 g; 0.2 mol) dissolved in water (10 ml) was added. The reaction mixture was refluxed for 30 minutes, then 2-chloromethyl-1,4-benzodioxane (37 g; 0.2 mol) dissolved in ethanol (100 ml). Boiling was continued for 90 additional minutes, then the mixture was left to stand overnight. Inorganic salts were filtered and solvent was evaporated under reduced pressure. The oily residue was treated with dichloromethane (300 ml) and extracted with 10% HCl. The combined acid layers were washed with ether, cooled, strongly alkalinized with 20% NaOH and again extracted with ether. The pooled ether extracts were washed with water, dried ($K_2CO_3$), filtered and evaporated, to give a nearly colourless oil (34.7 g; 77% yield) as a residue, which was used without additional purification.

Sulfur (Shoeniger): calc. 14.23%; found 14.51%.

(b) 1-(2-Mercaptoethyl-1-[2-(2-methylthioethyl)-1,4-benzodioxan]-2-nitro-ethene-1,1-diamine By reacting the previously prepared ethene-diamine with 2-(nitromethylene)thiazolidine, according to the procedure described in Example 1, compound (b) was obtained. Yield about 60%.

Sulfur (Shoeniger): calc. 17.26%; found 17.05%.

(c) Title compound

By reacting mercaptan (b) with 2-(dimethylaminomethyl)-5-chloromethylfuran in the presence of a base, according to the procedure described in Example 1, the title compound was obtained in 81% yield.

Elemental analysis: for $C_{23}H_{32}N_4O_5S$ (628.77); calc.%: C=43.93; H=5.13; N=8.91; S=10.20; found %: C=44.05; H=5.05; N=9.05; S=10.10.

EXAMPLE 7

N-Cyano-N'-[2-[[[5-(dimethylamino)methyl-2-furanyl]-methyl]thio]ethyl]-N'''-(2,4-dimethyl-1,8-naphthiridyl)-guanidine By reacting N-cyano-N'-[2-[[[5-(dimethylamino)-methyl]-2-furanyl]methyl]thio]-S-methyl-isothiourea and 7-amino-2,4-dimethyl-1,8-naphthiridine, as described in Example 2, title compound was obtained in a 54% yield.

Elemental analysis: for $C_{22}H_{27}N_7OS$ (437.57); calc.%: C=60.39; H=6.22; N=22.41; S=7.32; found %: C=60.46; H=6.15; N=22.50; S=7.57.

EXAMPLE 8

N-[2-[[[5-(Dimethylamino)methyl-2-furanyl]methyl]-thio]ethyl]-N'-(6-nitro-2-benzothiazolyl)-2-nitro-1,1-ethenediamine By reacting 1-[[[5-(dimethylamino)methyl-2-furanyl]methyl]thio]ethylamino]-2-methylthio-2-nitroethene with 2-amino-6-nitrobenzothiazole, according to the procedure described in Example 4, the product was obtained in a 58% yield.

Elemental analysis: for $C_{19}H_{22}N_6O_5S$ (446.49); calc.%: C=51.11; H=4.96; N=18.82; S=7.18; found %: C=51.27; H=5.05; N=18.90; S=7.22.

EXAMPLE 9

N-[2-[[[5-(Dimethylamino)methyl-2-furanyl]methyl]-thio]ethyl]-N'-[2-(benzimidazolyl-2-methyleneoxy)-ethyl]-2-nitro-1,1-ethenediamine

(a) N-(Benzymidazolyl-2-methoxyethyl)phthalimide

N-(2-Hydroxyethyl)phthalimide (19.1 g; 0.1 mol) was dissolved in tetrahydrofuran (300 ml), then sodium hydride (4 ml in 60% suspension in oil; 0.1 mol) was added. After heating to mild reflux for 30 minutes, 2-chloromethyl-benzoimidazole (16.7 g; 0.1 mol) dissolved in anhydrous tetrahydrofuran (50 ml) was added in about 60 minutes. The mixture was boiled for 2 hours, then left to stand overnight at room temperature and filtered. The filtrate was evaporated under reduced pressure, the obtained semisolid residue was dissolved in dichloromethane (200 ml) washed in turn with water, 2% HCl, water, 5% NaOH, dried (MgSO$_4$), filtered and evaporated.

The resulting residue (38.5 g; 87% yield) was used in the subsequent step without further purification.

(b) 2-(Benzimidazolyl-2-methyleneoxy)ethylamine

The previously prepared phthalimide (35 g; 0.08 mol) was dissolved in absolute ethanol; hydrazine hydrate (4 g; 0.08 mol) was added thereto. The mixture was left to stand for 2 days, then it was filtered from the separated phtalhydrazide and the filtrate was evaporated to dryness. The residue was taken up with dichloromethane, washed with water and extracted with 10% HCl. The acidic extracts were cooled, alkalinized with 20% NaOH and extracted with dichloromethane. The filtrate was dried, and evaporated under reduced pressure, to obtain a crude product (13.4 g; 87% yield) which was purified by silica gel chromatography, eluting with ethanol/triethylamine (9:1), (11.5 g; 74.7% yield).

(c) Title compound

By reacting 1-[[[[5-(dimethylamino)methyl-2-furanyl]methyl]thio]ethylamino]-1-methylthio-2-nitroethene with previously prepared 2-(benzimidazolyl-2-methyleneoxy)ethylamine, as described in Example 4, the title compound was obtained in 57% yield.

Elemental analysis: for $2_27H_{31}N_6O_4S$ (475.59); calc.%: C=55.56; H=6.57; N=17.67; S=6.74; found %: C=55.60; H=6.60; N=17.58; S=6.68.

EXAMPLE 10

N-[2-[[[5-(Dimethylamino)methyl-2-furanyl]methyl]thio]ethyl]-N'-[3-(2-benzooxazolyl-thio)propyl]-2-nitro-1,1-ethenediamine (a) 3-(2-Benzooxazolylthio)propylamine 2-Mercaptobenzoxazole (15.2 g; 0.1 mol) was dissolved in ethanol (200 ml); NaOH (4.0 g; 0.1 mol) dissolved in water was added thereto. The reaction mixture was refluxed for 30 minutes, then 3-chloropropylamine (9.3 g; 0.1 mol) dissolved in ethanol (50 ml) was added. The mixture was refluxed for 90 minutes, cooled, filtered from the salt and the solvent was evaporated under reduced pressure. The residue was purified by silica gel chromatography, eluting with methanol/ether (1:3), (15.0 g; 71.6% yield).

Sulfur (Schoeniger): calc. 15.32%; found 15.15%.

(b)
N-[3-(2-Benzooxazolylthio)propyl]-N'-(2-mercaptoethyl)-2-nitro-1,1-ethenediamine The desired compound was obtained by reacting the previously prepared propylamine with 2-(nitromethylene)thiazolidine, as described in Example 6.

Sulfur (Schoeniger): calc. 18.03%; found 17.89%.

(c) Title compound

By reacting the previously prepared ethenediamine with 2-(dimethylaminomethyl)-5-chloromethylfuran, as described in Example 1, the title compound was obtained.

Elemental analysis: for $C_{22}H_{30}N_5O_4S_2$ (492.63); calc.%: C=53.64; H=6.14; N=14.22; S=13.01; found %: C=53.54; H=5.98; N=14.19; S=12.95.

EXAMPLE 11

N-Cyano-N'-[2-[[[5-(Dimethylamino)methyl-2-furanyl]-methyl]thio]ethyl]-N''-/4-(2,4-dinitro-1-oxynaphthyl)-butyl]guanidine (a) 4-(2,4-Dinitronaphthyl-1-oxy)butylamine 2,4-Dinitronaphthole (23.49 g; 0.1 mol) was dissolved in 300 ml of ethanol, and NaOH (4.0 g; 0.1 mol) dissolved in water (5 ml) was added. The mixture was cooled to 0° C., then N-(4-bromobutyl)phthalimide (28.2 g; 0.1 mol) dissolved in the same solvent (100 ml) was added, without exceed a temperature of 5° C. The reaction mixture was refluxed for about 30 minutes, cooled, filtered from the separated NaBr and added with hydrazine monohydrate. After about 50 hours at room temperature, the separated phthalhydrazide was filtered, the filtrate was evaporated under reduced pressure and the semi-solid residue obtained was purified according to W. C. Still et al. (J. Org. Chem. 43, 2923-1978): (12.5 g; 41% yield).

Nitrogen: calc. 13.76%; found 13.87%.

(b) Title compound

By reacting N-cyano-N'-[2-[[[5-(dimethylamino)-methyl]furanyl]methyl]thio]ethyl]-S-methyl-isothiourea with the previously prepared butylamine, as described in Example 2, the title compound was obtained in a 67% yield.

Elemental analysis: for $C_{26}H_{31}N_7O_6S$ (569.65); calc.%: C=54.82; H=5.48; N=17.21; S=5.63; found %: C=54.53; H=5.15; N=17.30; S=5.49.

EXAMPLE 12

N-[2-[[[5-(Dimethylamino)methyl-2-furanyl]methyl]thio]ethyl]-N'-[3-(1-methoxyindanyl-2-oxy)propyl]-2-nitro-1,1-ethenediamine (a) 3-(1-Methoxyindanyl-2-oxy)propylamine By reacting 1-methoxyindanole with N-(3-bromopropyl)-phthalimide in absolute ethanol, in the presence of NaH, N-[1-(1-methoxyindanyl-2-oxy)propyl]-phthalimide which was treated with hydrazine analogously to the procedure described in Example 11, the desired compound was obtained in a 41% yield.

Nitrogen (Kjeldahl): calc. 6.26%; found 6.41%.

(b)
N-[3-(1-Methoxyindanyl-2-oxy)propyl]-N'-(2-mercaptoethyl)urea 3-(1-Methoxyindanyl-2-oxy)propylamine (22 g; 0.1 mol) was dissolved in anhydrous $CHCl_3$ (200 ml). The solution was stirred for 30 minutes at room temperature, then cysteamine (7.7 g; 0.1 mol) was added, without isolating the N-[3-(1-methoxyindanyl-2-oxy)-propyl]imidazolcarbonylamide). The reaction mixture was stirred for 30 additional minutes and filtered, the filtrate was washed in turn with water, 10% HCl, water and dried ($Na_2SO_4$). The solvent was evaporated. The obtained crude product was crystallized from ethanol/petroleum ether, yielding the analytically pure product (12.6 g; 41%).

Sulfur (Schoeniger): calc. 9.91%; found 9.78%.

(d)
N-[2-[[[5-(Dimethylamino)methyl-2-furanyl]methyl]thio]ethyl]-N'-[3-(1-methoxyindanyl-2-oxy)propyl]-urea 0.6 Grams (0.025 g.atom) of Na was dissolved in ethanol (100 ml), then N-[3-(1-methoxy-indolyl-2-oxy)-propyl]-N'-(2-mercaptoethyl)urea (8.1 g; 0.025 mols) previously prepared, was added. The reaction mixture was heated for 15 minutes under stirring, (2-dimethylaminomethyl)-5-chloromethylfuran (4.35 g; 0.025 mols) dissolved in absolute ethanol (20 ml) was slowly added, heating was continued at 70° C. for 2 hours. The reaction mixture was cooled, added with water till slight turbidity, left to stand overnight A crystalline product was obtained, which was directly used in the subsequent step (8.9 g; 71% yield).

Sulfur (Schoeniger): calc. 7.11%; found 6.91%.

(e) Title compound

Nitromethane (3.5 g; 2.7 ml; 0.05 mol) was placed in a flask cooled in ice-salt bath. To the reaction mixture were slowly added methanol (100 ml) and a previously cooled NaOH aqueous solution (2.1 g in 2.5 ml), not exceeding 10°-15° C. A precipitate formed which was stirred for 1 hour, diluted HCl was added till neutrality, then water till turbidity. The mixture was left to stand overnight, then a crystallyne was recovered which was recrystallized from aqueous ethanol (16.1 g; 64% yield).

Elemental analysis: for $C_{25}H_{35}N_4O_5S$ (503.65); calc.%: C=59.62; H=7.00; N=11.12; S=6.36; found %: C=59.39; H=6.84; N=10.95; S=6.24.

EXAMPLE 13

N-Cyano-N'-[2-[[[5-(dimethylamino)methyl-2-furanyl]methyl]thio]ethyl]-N''-[2-(1-naphthyl)ethyl]quanidine By reacting (+)-1-(1-naphthyl)ethylamine with N-cyano-N'-[2-[[[5-(dimethylamino)methyl-2-furanyl]methyl]thio]ethyl]-S-methyl-isothiourea, as described in Example 2, the desired compound was obtained in 64% yield.

Elemental analysis: for $C_{24}H_{29}N_5OS$ (435.59); calc.%: C=66.17; H=6.71; N=16.07; S=7.36; found %: C=66.28; H=6.83; N=15.96; S=7.20.

EXAMPLE 14

N-[2-[[[5-(Dimethylamino)methyl-furanyl]methyl]thio]-ethyl]-N'-[3-(1,2,3,4-tetrahydronaphthyl-1-oxy)-propyl]-2-nitro-1,1-ethenediamine (a) 3-(1,2,3,4-Tetrahydronaphthyl-1-oxy)propylamine By reacting α-tetralol with N-(3-bromopropyl)phthalimide in the presence of a strong base, according to the procedure described in Example 11, N-[1-(1,2,3,4-tetrahydronaphthyl-1-oxy)propyl]phthalimide was obtained, which was treated with hydrazine to give the desired propylamine in a 57% yield.

Nitrogen (Kjeldahl): calc. 6.82%; found 6.77%.

(b) Title compound

By reacting propylamine (a) with 1-[[[[5-(dimethylamino)methyl]-furanyl]methyl]thio]ethylamino]-1-(methylthio)-2-nitroethene according to the procedure described in Example 4, the title compound was obtained in a 59% yield.

Elemental analysis: for $C_{25}H_{36}N_4O_4S$ (488.66); calc.%: C=61.45; H=7.42; N=11.46; S=6.56; found %: C=61.54; H=7.33; N=11.27; S=6.44.

EXAMPLE 15

N-[2-[[[5-(Dimethylamino)methyl-2-furanyl]methyl]thio]ethyl]-N'-[2-[[2-(2,3-dihydrobenzofuranyl)methyl]thio]ethyl]-1,1-ethenediamine (a) 2-[2-(2,3-Dihydrobenzofuranyl)methyl]thio]ethylamine Compound (a) was obtained by reacting 2-(chloromethyl)-2,3-dihydrobenzofuran with cysteamine, according to the procedure described in Example 6.

Sulfur (Schoeniger): calc. 15.31%; found 15.10%.

(b) Title compound

It was obtained as described in Example 4, starting from amine (a), in a 74% yield.

Elemental analysis: for $C_{17}H_{32}N_4O_4S_2$ (540.71); calc.%: C=59.98; H=5.97; N=10.36; S=11.86; found %: C=60.12; H=5.83; N=10.28; S=11.65.

EXAMPLE 16

N-[2-[[[5-(Dimethylamino)methyl-2-furanyl]methyl]thio]ethyl]-N'-[2-(3-indolyl)ethyl]-2-nitro-1,1-ethenediamine The desired compound was obtained according to the procedure described in Example 4, starting from 3-(2-aminoethyl)indole, in a 60% yield.

Elemental analysis: for $C_{22}H_{29}N_5O_3S$ (443.57) calc.%: C=59.57; H=6.59; N=15.78; S=7.23; found %: C=59.34; H=6.60; N=15.71; S=7.10.

EXAMPLE 17

N-[2-[[[5-(Dimethylamino)methyl-2-furanyl]methyl]thio]ethyl]-N'-[3-(benzimidazolyl-2-thio)propyl]-2-nitro-1,1-ethenediamine (a) 3-(Benzimidazolyl-2-thio)propylamine The desired compound was obtained, according to the procedure described in Example 3, by reacting benzimidazole-2-thiol with 3-chloropropylamine in the presence of a base. Yield 84%.

Sulfur (Schoeniger): calc. 15.39%; found 15.43%.

(b) Title compound

According to the procedure of Example 4, title compound was obtained in a 70% yield, starting from propylamine (a).

Elemental analysis: for $C_{22}H_{31}N_6O_3S$ (491.65); calc.%: C=53.74; H=6.36; N=17.10; found %: C=53.55; H=6.30; N=16.88.

EXAMPLE 18

N-[2-[[[5-(Dimethylamino)methyl-2-furanyl]methyl]thio]ethyl]-N'-[[4-(5-nitrobenzimidazolyl)-2-thiobutyl]-2-nitro-1,1-ethenediamine The procedure of Example 17 was repeated, starting from 4-(5-nitrobenzimidazolyl-2-thio)butylamine, to give the desired compound.

Elemental analysis: for $C_{22}H_{29}N_7O_5S_2$ (535.64); calc.%: C=49.33; H=5.46; N=18.30; S=11.97; found %: C=49.44; H=5.38; N=18.12; S=12.05.

EXAMPLE 19

N-[2-[[[5-(Dimethylamino)methyl-2-furanyl]methyl]thio]ethyl]-N'-[[2-(benzothiazolyl)-2-oxy]ethyl]-2-nitro-1,1-ethenediamine The procedure of Example 11 was repeated, to give 2-(benzothiazolyl-2-oxy)ethylamine, which was reacted as described in Example 4, obtaining the desired compound in a 59% yield.

Elemental analysis: for $C_{21}H_{28}N_5O_4S$ (478.61); calc.%: C=52.70; H=5.89; N=14.63; S=13.40; found %: C=52.50; H=5.63; N=14.71; S=13.34.

EXAMPLE 20

N-[2-[[[5-(Dimethylamino)methyl-2-furanyl]methyl]thio]ethyl]-N'-[2-(3-indolyl)ethyl]-2-nitro-1,1-ethenediamine The procedure of Example 4 was repeated, starting from 2-(3-indolyl)ethylamine, to obtain the title compound.

According to the same procedure the following compounds were prepared:

N-[2-[[[5-(dimethylamino)methyl-2-furanyl]methyl]-thio]ethyl]-N'-[2-(3-indolyl)propyl]-2-nitro-1,1-ethenediamine;

N-[2-[[[5-(dimethylamino)methyl-2-furanyl]methyl]-thio]ethyl]-N'-[2-(3-indolyl)butyl]-2-nitro-1,1-ethenediamine.

The elemental analysis data confirm the structure of said compounds.

EXAMPLE 21

N-Cyano-N'-[2-[[[5-(dimethylamino)methyl-2-furanyl]methyl]thio]ethyl]-N''-[2-(5-methylbenzofuryl)ethyl]-guanidine (a) 2-(5-Methylbenzofuryl)ethylamine 5-Methylbenzofuryl-3-acetic acid was treated with $SOCl_2$ in benzene, then with ammonia; the obtained 5-methylbenzofuryl-3-acetamide was reduced with $LiAlH_4$ in tetrahydrofuran, to give the desired amine. Yield: 38% with respect to the starting acid.

Nitrogen (Kjeldahl): calc. 8.04%; found 7.93%.

(b) Title compound

It was obtained by reacting amine (a) with N-cyano-N'-[2-[[[5-(dimethylamino)methyl-2-furanyl]-methyl]-thio]ethyl]-S-methyl-isothiourea, as described in Example 2.

Elemental analysis: for $C_{23}H_{28}N_5O_2S$ (438.57); calc.%: C=62.99; H=6.43; N=15.97; S=7.31; found %: C=70.15; H=6.55; N=16.07; S=7.22.

EXAMPLE 22

N-[2-[[[5-(Dimethylamino)methyl-2-furanyl]methyl]-thio]-ethyl]-N'-[2-(4-chloro-benzothiazolyl)]-2-nitro-1,1-ethenediamine It was prepared according to the procedure described in Example 4, starting from 2-amino-4-chloro-benzothiazole. Yield: 77%.

Elemental analysis: for $C_{19}H_{23}ClN_5O_3S_2$ (469.00); calc.%: C=48.66; H=4.94; N=14.93; S=13.08; found %: C=48.80; H=4.80; N=15.12; S=12.87.

EXAMPLE 23

N-Cyano-N'-[2-[[[5-(dimethylamino)methyl-2-furanyl]methyl]thio]ethyl]-N''-(6-methoxybenzothiazolyl)-guanidine It was prepared according to the procedure described in Example 2, starting from 6-methoxy-2-aminobenzothiazole. Yield: 58%.

Elemental analysis: for $C_{20}H_{25}N_6O_2S_2$ (445.58); calc.%: C=53.91; H=5.65; N=18.86; S=14.39; found %: C=53.76; H=5.60; N=18.73; S=14.53.

EXAMPLE 24

N-[2-[[[5-(Dimethylamino)methyl-2-furanyl]methyl]-thio]ethyl]-N'-[2-(6,7-dimethoxy-1,2,3,4-tetrahydro-1-isoquinolyl)ethyl]-2-nitro-1,1-ethenediamine It was obtained according to the procedure described in Example 4, starting from 1-(2-aminoethyl)-6,7-dimethoxy-1,2,3,4-tetrahydro-isoquinoline. Yield: 69%.

Elemental analysis: for $C_{25}H_{36}N_5O_5S$ (518.67); calc.%: C=57.89; H=6.99; N=13.50; S=6.18; found %: C=58.00; H=7.05; N=13.62; S=6.22.

EXAMPLE 25

N-[2-[[[5-(Dimethylamino)methyl-2-furanyl]methyl]-thio]ethyl]-N'-[3-[1,2,3,4-tetrahydro-isoquinolyl-2-ethyloxy)propyl]-2-nitro-1,1-ethenediamine (a) 3-(1,2,3,4-Tetrahydro-isoquinolyl-2-ethyloxy)propylamine The desired amine was prepared according to the procudure used for the above cited amines, by reacting N-(2-hydroxyethyl)-1,2,3,4-tetrahydro-isoquinoline with N-(3-bromopropyl)phthalimide and treating the resulting compound with hydrazine. Yield: 47%.

Nitrogen (Kjeldahl): calc. 11.95%; found 11.73%.

(b) Title compound

It was prepared according to the procedure described in Example 4. Yield: 62%.

Elemental analysis: for $C_{26}H_{39}N_5O_4S$ (517.70); calc.%: C=60.32; H=7.59; N=13.52; S=6.19; found %: C=60.15; H=7.39; N=13.44; S=6.05.

EXAMPLE 26

N-[2-[[[5-(Dimethylamino)methyl-2-furanyl]methyl]-thio]ethyl]-N'-[2-(1,4-benzodioxan-7-methylthio)-ethyl]-2-nitro-1,1-ethenediamine (a) 2-(1,4-Benzodioxan-7-methylthio)ethylamine It was obtained by reacting 7-(chloromethyl)-1,4-benzodioxane (prepared according to G. Baddeley and N. H. Smith (J. Org. Chem. 1961, 2516)) with cysteamine, in the presence of a base, as described in Example 4. Yield: 68%.

Sulfur (Schoeniger): calc. 14.22%; found 14.16%.

(b) Title compound

It was obtained according to the procedure of Example 4, in a 59% yield.

Elemental analysis: for $C_{23}H_{32}N_4O_5S_2$ (508.66); calc.%: C=54.31; H=6.34; N=11.01; S=12.60; found %: C=54.14; H=6.21; N=10.90; S=12.47.

Starting from intermediate described in (a), according to the procedure of Example 2, N-cyano-N'-[2-[[[5-(dimethylamino)methyl-2-furanyl]methyl]thio]-ethyl-N''-[2-(1,4-benzodioxane-7-methylthio)ethyl]guanidine was also obtained.

Elemental analysis: for $C_{23}H_{31}N_5O_3S_2$ (489.66) calc.%: C=56.41; H=6.38; N=14.30; S=13.09; found %: C=56.55; H=6.60; N=14.32; S=13.00.

EXAMPLE 27

N-[2-[[[5-(Dimethylamino)methyl-2-furanyl]methyl]-thio]ethyl]-N'-[2-(1,4-benzodioxane-7-methyloxy)-ethyl]-2-nitro-1,1-ethenediamine (a) 2-(1,4-Benzodioxane-7-methyloxy)ethylamine By reacting 7-(chloromethyl)-1,4-benzodioxane with N-(2-hydroxyethyl)phthalimide and subsequently treating the resulting compound with hydrazine, as described in Example 5, the desired intermediate was prepared in a 44% yield.

Nitrogen (Kjeldahl): calc. 6.69%; found 6.54%.

(b) Title compound

It was obtained according to the procedure described in Example 2 with amine (a). Yield: 73%.

Elemental analysis: for $C_{23}H_{32}N_4O_6S$ (492.60); calc.%: C=56.07; H=6.55; N=11.37; S=6.50; found %: C=55.89; H=6.34; N=11.12; S=6.65.

Starting from amine (a), according to the procedure described in Example 2, N-cyano-N'-[2-[[[5-(dimethylamino)methyl-2-furanyl]methyl]thio]ethyl]-N''-[2-(1,4-benzodioxan-7-methyloxy)ethyl]guanidine was obtained. Yield: 68%.

Elemental analysis: for $C_{23}H_{31}N_5O_4S$ (473.60); calc.%: C=58.33; H=6.60; N=14.79; S=6.77; found %: C=58.13; H=6.70; N=14.63; S=6.80.

EXAMPLE 28

N-[2-[[[5-(Dimethylamino)methyl-2-furanyl]methyl]thio]ethyl]-N'-[3-[2-(1,4-benzodioxan)propyl]-2-nitro-1,1-ethenediamine By reacting 3-(2-(1,4-benzodioxane)propylamine with 2-(nitromethylene)thiazolidine, N-2-[2-(1,4-benzodioxan)propyl]-N'-(2-mercaptoethyl)-2-nitro-1,1-ethenediamine (sulfur (Schoeniger) calc.: 9.45%; found: 9.28%) was obtained, which was subsequently reaced with 2-(dimethylaminomethyl)-5-chloromethylfuran, according to the procedure of Example 3, to give title compound. Yield: 48%.

Elemental analysis: for $C_{23}H_{32}N_4O_5S$ (476.60); calc.%: C=57.96; H=6.77; N=11.76; S=6.73; found %: C=57.34; H=6.70; N=11.68; S=6.58.

EXAMPLE 29

N-Cyano-N'-[2-[[[5-(dimethylamino)methyl-2-furanyl]methyl]thio]ethyl]-N''-[2-(1,3-benzodioxan-6-chloro-8-methylthio)ethyl]guanidine (a) 2-(1,3-Benzodioxane-6-chloro-8-methylthio)ethylamine By reacting 6-chloro-8-(iodomethyl)-1,3-benzodioxane (P. Mamalis, J. Chem. Soc. 1960, 4747), with cysteamine, according to the procedure described in Example 4, intermediate (a) was obtained in a 79% yield.

Nitrogen (Kjeldahl): calc. 5.39%; found 5.25%.

(b) Title compound

It was obtained according to the procedure described in Example 2, starting from the previously prepared amine (a). Yield: 62%.

Elemental analysis: for $C_{232}H_{30}ClN_5O_3S_2$ (524.10); calc.%: C=52.71; H=5.77; N=13.36; S=12.23; found %: C=52.60; H=5.70; N=13.15; S=12.03.

EXAMPLE 30

N-Cyano-[2-[[[5-(dimethylamino)methyl-2-furanyl]methyl]thio]ethyl]-N''-[2-(7-methoxyphthalazine-1-oxy)ethyl]guanidine (a) 2-(7-methoxyphthalazin-1-oxy)ethylamine The procedure of Example 5 was repeated, starting from 1-chloro-7-methoxyphthalazine, to give intermediate (a) in a 58% yield.

Elemental analysis: for $C_{11}H_{13}N_3O_2$ (219.24); calc.%: C=60.26; H=5.97; N=19.16; found %: C=60.15; H=5.88; N=19.05.

(b) Title compound

It was prepared according to the procedure described in Example 5. Yield: 71%.

Elemental analysis: for $C_{13}H_{29}N_7O_3S$ (483.59); calc.%: C=57.12; H=6.04; N=20.27; S=6.63; found %: C=56.98; H=6.00; N=20.10; S=6.71.

EXAMPLE 31

N-[2-[[[5-(Dimethylamino)methyl-2-furanyl]methyl]thio]ethyl]-N'-[2-(quinuclidyl-3-methyloxy)ethyl]-2-nitro-1,1-ethenediamine (a) 2-(Quinuclidyl-3-methyloxy)ethylamine It was prepared by reacting 3-(hydroxymethyl)-quinuclidine with N-(2-bromoethyl)phthalimide, in non-polar solvent in the presence of a strong base, and subsequently of the amino group with hydrazine, according to the procedure described in Example 11. Yield: 53%.

Elemental analysis: for $C_{10}H_{20}N_2O$ (184.28); calc.%: C=65.17; H=10.94; N=15.20; found %: C=64.93; H=10.71; N=15.15.

(b) Title compound

It was obtained as described in Example 4, in a 73% yield.

Elemental analysis: for $C_{22}H_{37}N_4O_4S$ (453.63); calc.%: C=58.25; H=8.22; N=12.35; S=7.07; found %: C=58.05; H=8.00; N=12.48; S=7.15.

EXAMPLE 32

N-[2-[[[5-(Dimethylamino)methyl-2-furanyl]methyl]thio]ethyl]-N'-[3-[bicyclo(2,2,1)heptan-2-methyloxy]propyl]-2-nitro-1,1-ethenediamine (a) 3-[Bicyclo(2,2,1)heptan-2-methyloxy]propylamine Bicyclo(2,2,1)heptan-2-carbinol (12.6 g; 0.1 mol) was dissolved in toluene (200 ml), then NaH (0.1 mol) was added, the mixture was refluxed for 1 hour, then 3-bromopropylamine (13.8 g; 0.1 mol) diluted in toluene (50 ml) was slowly added, in the heat. Boiling was continued for 2 hours, then the reaction mixture was cooled, inorganic salts were filtered and the filtrate was evaporated under reduced pressure, to give a residue which was purified by silica gel chromatography, eluting with ethanol/ether (1:1). The pure product was obtained (15.3 g; 83% yield).

Nitrogen (Kjeldahl): calc. 7.60%; found 7.45%.

(b) Title compound

It was obtained as described in Example 4, in a 58% yield.

Elemental analysis: for $C_{23}H_{39}N_4O_4S$ (467.65); calc.%: C=59.07; H=8.41; N=11.98; S=6.85; found %: C=59.18; H=8.66; N=12.10; S=6.77.

EXAMPLE 33

N-[2-[[[5-(Dimethylamino)methyl-2-furanyl]methyl]thio]ethyl]-N'-[2-(1-adamantyl)ethyloxy)ethyl]-2-nitro-1,1-ethenediamine (a) 2-[2-(1-Adamantyl)ethyloxy]ethylamine The desired intermediate was obtained, according to the procedure of Example 11, starting from 1-(2-hydroxyethyl)adamantane. Yield: 46%.

(b) Title compound

It was obtained according to the procedure of Example 4.

Elemental analysis: for $C_{26}H_{42}N_4O_4S$ (506.72); calc.%: C=61.63; H=8.35; N=11.06; S=6.33; found %: C=61.37; H=8.18; N=11.20; S=6.10.

EXAMPLE 34

N-Cyano-N'-[2-[[[5-(dimethylamino)methyl-2-furanyl]-methyl]thio]ethyl]-N"-(pinan-methyl)guanidine It was obtained as described in Example 2, starting from pinan-methylamine. Yield: 66%.

Elemental analysis: for $C_{23}H_{37}N_5OS$ (431.65) calc.%: C=63.99; H=8.64; N=16.23; S=7.43; found %: C=63.82; H=8.48; N=16.10; S=7.18.

EXAMPLE 35

N-[2-[[[5-(Dimethylamino)methyl-2-furanyl]methyl]-thio]-ethyl]-N'-[2-(2-norbornyl)ethyl]-2-nitro-1,1-ethenediamine

(a) 2-(2-Norbornyl)ethylamine

Norbornane-2-acetic acid was treated with $SOCl_2$, then with $NH_3$. The resulting amine was reduced with $LiAlH_4$ to give the desired intermediate. Yield: 35%.

Elemental analysis: for $C_{29}H_{17}N$ (139.24); calc.%: C=77.63; H=12.31; N=10.06; found %: C=77.60; H=12.20; N=9.97.

(b) Title compound

It was obtained according to Example 4, in a 77% yield.

Elemental analysis: for $C_{21}H_{34}N_4O_3S$ (422.59); calc.%: C=59.69; H=8.11; N=13.26; S=7.58; found %: C=59.58; H=8.05; N=13.33; S=7.37.

EXAMPLE 36

N-[2-[[[5-(Dimethylamino)methyl-2-furanyl]methyl]-thio]ethyl]-N'-[2-(6,6-dimethylbicyclo(3,1,1)ept-2-ene-2-ethyloxy)ethyl]-2-nitro-1,1-ethenediamine

(a) 2-[6,6-Dimethylbicyclo(3,1,1)ept-2-ene-2-ethyloxy]ethylamine

It was prepared by reacting 2-hydroxyethyl-6,6-dimethylbicyclo(3,1,1)ept-2-ene with N-(2-bromoethyl)-phthalimide, according to Example 11. Yield: 49%.

Nitrogen (Kjeldahl): calc. 6.69%; found 6.48%.

(b) Title compound

It was obtained according to Example 4, in a 82% yield.

Elemental analysis: for $C_{25}H_{40}N_4O_4S$ (492.69); calc.%: C=60.95; H=8.18; N=11.37; S=6.51; found %: C=61.05; H=8.27; N=11.30; S=6.31.

EXAMPLE 37

N-Cyano-N'-[2-[[[5-(dimethylamino)methyl-2-furanyl]-methyl]thio]ethyl]-N"-[2-(3,4-dihydroisoquinolyl-6,7-dimethoxy-1-methylthio)ethyl]guanidine

(a) 2-(3,4-Dihydroisoquinolyl-6,7-dimethoxy-1-methylthio)ethylamine

It was obtained according to the procedure described in Example 6, by reacting 1-(chloromethyl)-6,7-dimethoxy-3,4-dihydroisoquinoline (F. Benington and R. D. Morin, J. Org. Chem. 26, 194 (1961) with cysteamine. Yield: 80%.

Nitrogen (Kjeldahl): calc. 11.43%; found 11.29%.

(b) Title compound

It was obtained according to the procedure of Example 2. Yield: 67%.

Elemental analysis: for $C_{26}H_{36}N_6O_3S_2$ (544.74); calc.%: C=57.33; H=6.66; N=15.43; S=11.77; found %: C=57.22; H=6.80; N=15.40; S=11.53.

EXAMPLE 38

N-Cyano-N'-[2-[[[5-(dimethylamino)methyl-2-furanyl]-methyl]thio]ethyl]-N"-[2-[3-(1-decahydroquinolyl)-propyloxy]ethyl]guanidine

(a) 2-[3-(1-Decahydroquinolyl)propyloxy]ethylamine

It was obtained as described in Example 5, starting from 1-(3-chloropropyl)decahydroquinoline (A. P. Gray, D. E. Heitmeier, C. J. Cavallito (J. Am. Chem. Soc. 81, 728 (1959)). Yield: 48%.

Elemental analysis: for $C_{15}H_{28}N_2O$ (252.40); calc.%: C=71.38; H=11.18; N=11.09; found %: C=71.05; H=11.10; N=11.13.

(b) Title compound

It was obtained according to the procedure of Example 2, in a 72% yield.

Elemental analysis: for $C_{27}H_{44}N_6O_2S$ (516.75); calc.%: C=62.75; H=8.58; N=16.26; S=6.20; found %: C=62.50; H=8.35; N=16.10; S=6.32.

EXAMPLE 39

N-Cyano-N'-[2-[[[5-(Dimethylamino)methyl-2-furanyl]-methyl]thio]ethyl]-N"-[2-(quinolyl-6-methyl-thio)-ethyl]guanidine

(a) 2-(Quinolyl-6-methylthio)ethylamine

It was prepared, according to the procedure of Example 6, starting from 6-(chloromethyl)quinoline (B. P. Lugovkin, C. A. 51 (1959)). Yield: 74%.

Sulfur (Schoeniger): calc. 14.68%; found 14.73%.

(b) Title compound

It was obtained according to the procedure of Example 2. Yield: 67%.

Elemental analysis: for $C_{24}H_{30}N_6OS_2$ (482.67); calc.%: C=59.72; H=6.26; N=17.41; S=13.28; found %: C=59.66; H=6.12; N=17.38; S=13.16.

EXAMPLE 40

N-[2-[[[5-(Dimethylamino)methyl-2-furanyl]methyl]-thio]ethyl]-N'-[2-(2,3-dihydrobenzofuranyl-2-methyloxy)ethyl]-2-nitro-1,1-ethenediamine

(a) 2-(2,3-Dihydrobenzofuranyl-2-methyl-5-methyloxy)-ethylamine

It was obtained starting from 5-(chloromethyl)-2-methyl-2,3-dihydrobenzofuran (G. Baddeley and H. A. Vickers, J. Chem. Soc. 1958, 4665), according to the procedure of Example 9. Yield: 38%.

Nitrogen (Kjeldahl): calc. 6.75%; found 6.90%.

(b) Title compound

It was obtained according to the procedure of Example 4. Yield: 67%.

Elemental analysis: for $C_{24}H_{34}N_4O_5S$ (490.62); calc.%: C=58.75; H=6.98; N=11.42; S=6.53; found %: C=58.80; H=7.05; N=11.55; S=6.43.

EXAMPLE 41

N-[2-[[[5-(Dimethylamino)methyl-2-furanyl]methyl]-thio]ethyl]-N'-[2-[3-(thionaphthenyl)methyloxy]ethyl]-2-nitro-1,1-ethenediamine (a) 2-[3-(Thionaphthenyl)methyloxy]ethylamine It was obtained from 3-(chloromethyl)thionaphthene (H. B. Chapman and A. J. Tompsett, J. Chem. Soc. 1961, 1291), according to the procedure of Example 5. Yield: 47%.

Nitrogen (Kjeldahl): calc. 15.46%; found 15.29%.

(b) Title compound

It was obtained according to the procedure of Example 4. Yield: 72%.

Elemental analysis: for $C_{23}H_{30}N_4S_2$ (490.64); calc.%: C=56.30; H=6.16; N=11.42; S=13.07; found %: C=56.55; H=6.20; N=11.30; S=12.95.

EXAMPLE 42

N-Cyano-N'-[2-[[[5-(Dimethylamino)methyl-2-furanyl]-methyl]thio]ethyl]-N''-[2-[2-[(5-methylbenzimidazolyl)-2-propyl]-2-thio]ethyl]-guanidine (a) 2-[2-[(5-Methylbenzymidazolyl)-2-propyl]2-thio]-ethylamine It was prepared by reacting 2-(2-chloropropyl)-5-methylbenzimidazole (W. R. Siegart and A. R. Day, J. Am. Chem. Soc. 79, 4391 (1957)) with cysteamine, as described in Example 6. Yield: 83%.

Nitrogen (Kjeldahl): calc. 12.80%; found 12.72%.

(b) Title compound

It was prepared as described in Example 2. Yield: 68%.

Elemental analysis: for $C_{25}H_{36}N_7OS$ (482.68); calc.%: C=62.21; H=7.52; N=20.31; S=6.64; found %: C=62.05; H=7.33; N=20.22; S=6.50.

(c) According to the same procedure, N-cyano-N'-[2-[[[5-(dimethylamino)methyl-2-furanyl]methyl]thio]-ethyl]-N''-[2-[2-[(5-nitrobenzimidazolyl)-1-ethyl]-1-thio]ethyl]guanidine was obtained, in a 74% yield. Intermediate 2-[2-[(5-nitrobenzimidazolyl)-1-ethyl]-1-thio]ethylamine was obtained in a 70% yield. (Sulfur (Schoeniger): calc. 11.99%; found 11.70%)) from 2-(1-chloroethyl)-5-nitrobenzymidazole (W. R. Siegart and A. R. Day, ibidem).

Elemental analysis: for $C_{23}H_{31}N_8O_3S_2$ (531.69) calc.%: C=51.96; H=5.87; N=21.07; S=12.06; found %: C=51.73; H=5.69; N=20.87; S=11.85.

EXAMPLE 43

N-[2-[[[5-(Dimethylamino)methyl-2-furanyl]methyl]-thio]ethyl]-N'-[2-[2-[(5-chlorobenzimidazolyl)-2-propyl]-2-thio]ethyl]-2-nitro-1,1-ethenediamine (a) 2-[2-[(5-Chlorobenzimidazolyl)-2-propyl]-2-thio]-ethylamine It was obtained according to the procedure described in Example 5, starting from 2-(2-chloropropyl)-5-chlorobenzymidazole (W. R. Siegart and A. R. Day, ibidem).

Nitrogen (Kjeldahl): calc. 5.48%; found 5.56%.

(b) Title compound

It was obtained as described in Example 4. Yield: 64%.

Elemental analysis: for $C_{24}H_{34}ClN_6O_4S$ (538.09); calc.%: C=53.57; H=6.37; N=15.62; S=5.96; found %: C=53.30; H=6.23; N=15.68; S=5.69.

(c) According to the same procedure, N-[2-[[[5-(dimethylamino)methyl-2-furanyl]methyl]thio]ethyl]-N'-[2-[2-(5-chlorobenzimidazolyl)-1-ethyl]-1-oxy]ethyl]-2-nitro-1,1-ethenediamine was obtained in a 71% yield. Intermediate 2-[2-(5-chlorobenzimidazolyl)-1-ethyl]-1-oxy]ethylamine was prepared from 2-(1-chloroethyl)-5-chlorobenzymidazole, in a 46% yield.

EXAMPLE 44

N-[2-[[[5-(Dimethylamino)methyl-2-furanyl]methyl]-thio]ethyl]-N'-[2-[(6-methylcumarinyl)methyloxy)-ethyl]-2-nitro-1,1-ethenediamine (a) 2-[(6-Methylcumarinyl)methyloxy]ethylamine It was obtained from 4-chloromethyl-6-methylcumarine, according to the procedure described in Example 5, in 52% yield.

Nitrogen (Kjeldahl): calc. 6.00%; found 5.82%.

(b) Title compound

It was prepared according to the procedure of Example 4, in a 59% yield.

Elemental analysis: for $C_{25}H_{32}N_4O_6S$ (516.62); calc.%: C=58.12; H=6249; N=10.84; S=6.20; found %: C=57.85; H=6.00; N=10.64; S=6.05.

EXAMPLE 45

N-[2-[[[5-(Dimethylaino)methyl-2-furanyl]methyl]-thio]ethyl]-N'-[3-(6-ethoxybenzothiazolyl)-2-thio[propyl]-2-nitro-1,1-ethenediamine (a) 3-[(6-Ethoxybenzothiazolyl)-2-thio]propylamine It was prepared from 6-ethoxy-2-mercaptobenzothiazole and 3-bromopropylamine, according to the procedure of Example 10. Yield: 77%.

Sulfur (Schoeniger): calc. 23.80%; found 23.77%.

(b) Title compound

It was obtained according to the procedure described in Example 4, in a 62% yield.

Elemental analysis: for $C_{24}H_{34}N_5O_4S_3$ (552.75); calc.%: C=52.15; H=6.20; N=12.67; S=17.40; found %: C=51.89; H=6.05; N=12.45; S=17.22.

EXAMPLE 46

N-[2-[[[5-(Dimethylamino)methyl-2-furanyl]methyl]-thio]ethyl]-N'-[3-[4-[7-(trifluoromethyl)quinolinyl]-thio]propyl]-2-nitro-1,1-ethenediamine (a) 3-[4-[7-(Trifluoromethyl)quinolinyl]thio]propylamine It was obtained according to the procedure of Example 10, by reacting 7-trifluuoromethyl-4-quinolinethiole with 3-chloropropylamine, in a 86% yield.

Elemental analysis: for $C_{13}H_{13}F_3N_2$ S (286.31); calc.%: C=54.53; H=4.57; N=9.78; found %: C=52.56; H=4.40; N=9.55.

(b) Title compound

It was prepared according to Example 4, in a 67% yield.

Elemental analysis: for $C_{25}H_{30}F_3O_3S_2$ (569.66); calc.%: C=52.71; H=5.31; N=12.29; S=11.25; found %: C=52.56; H=5.05; N=12.21; S=11.04.

EXAMPLE 47

N-Cyano-N'-[2-[[[5-(Dimethylamino)methyl-2-furanyl]-methyl]thio]ethyl]-N''-[[6-(2-diethylamino)ethoxy]-2-thiobenzothiazolyl]methyl]guanidine (a)

[6-[2-(Diethylamino)ethoxy]-2-thiobenzothiazolyl]methylamine

It was obtained by reacting 2-chloromethylmercapto-6-[2-(diethylamino)ethoxy]benzothiazole and by hexamethylenetetramine, according to the procedure described by A. T. Bottini et al. (Org. Synth. coll. vol. V, pag. 121), in a 48% yield.

Elemental analysis: for $C_{14}H_{22}N_3OS_2$ (312.47); calc.%: C=53.81; H=7.10; N=13.45; found %: C=53.72; H=7.00; N=13.50.

(b) Title compound

It was prepared as described in Example 4. Yield: 62%.

Elemental analysis: for $C_{26}H_{38}N_7O_2S_3$ (576.83) calc.%: C=54.14; H=6.64; N=16.99; S=16.67; found %: C=54.32; H=6.75; N=17.05; S=16.46.

EXAMPLE 48

N-Cyano-N'-[2-[[[5-(dimethylamino)methyl-2-furanyl]-methyl]thio]ethyl]-N''-[3,4-methylenedioxybenzyl]-guanidine It was obtained by reacting N-cyano-N'-[2-[[[5-(dimethylamino)methyl-2-furanyl]methyl]thio]ethyl]-S-(methyl)isothiourea, prepared according to Example (2c) with piperonylamine in benzene, as described in Example 2.

Elemental analysis: for $C_{20}H_{25}N_5O_3S$ (415.51); calc.%: C=57.81; H=6.06; N=16.85; found %: C=57.05; H=5.87; N=16.31.

I claim:

1. A compound selected from the group consisting of
(a) a furan derivative of the formula:

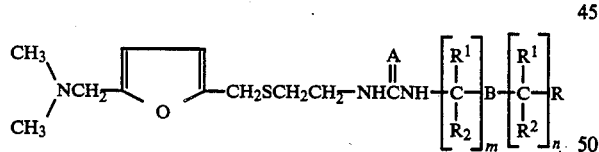

wherein

A is =CHNO$_2$ or =NCN;

B is —CH$_2$—, —S—, —O—, or a direct bond;

each of R$^1$ and R$^2$, independently of the other, is hydrogen or alkyl of 1 to 4 carbon atoms;

each of n and m, independently of the other, has a value of 0, 1, 2, 3, or 4; and R is the monovalent radical derived from a polycyclic selected the group consisting of

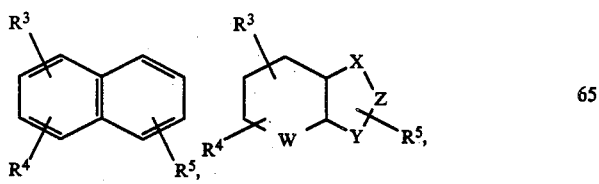

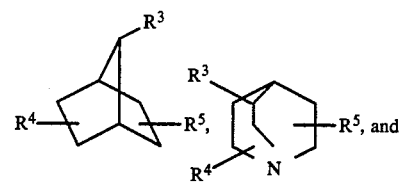

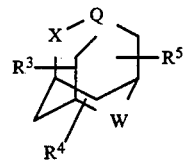

in which each of R$^3$, R$^4$, and R$^5$, independently of the other, is hydrogen; halo; nitro; hydroxy; alkyl of 1 to 4 carbon atoms which is unsubstituted or substituted with nitro, hydroxy, mercapto, halo, amino, C$_1$-C$_4$ alkylamino or C$_1$-C$_4$ dialkylamino, piperidino, pyrrolidino, piperazino, or morpholino, or the chain of which group is interrupted with oxygen, sulfur or nitrogen; alkenyl of 2 to 4 carbon atoms which is unsubstituted or substituted with nitro, hydroxy, mercapto, halo, amino, C$_1$-C$_4$ alkylamino or C$_1$-C$_4$ dialkylamino, piperidino, pyrrolidino, piperazino, or morpholino, or the chain of which group is interrupted with oxygen, sulfur or nitrogen;

alkynyl of 2 to 4 carbon atoms; alkoxy of 1 to 4 carbon atoms; or alkylthio of 1 to 4 carbon atoms;

W is —O—, —S—, —CH$_2$—, or —NH—;

each of X, Y, and Z independently of the other is —O—, —S—, —CH$_2$—, —NH—, or —CH$_2$CH$_2$— and Q is —N= or —CH=;

(b) the pharmaceutically acceptable acid addition salts thereof; and (c) the hydrates thereof.

2. A compound according to claim 1 wherein R is

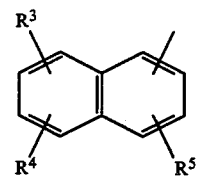

3. A compound according to claim 1 wherein R is

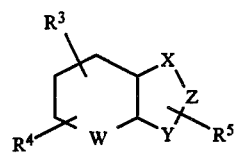

4. A compound according to claim 1 wherein R is

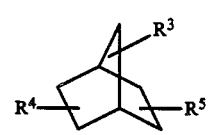

5. A compound according to claim 1 wherein R is

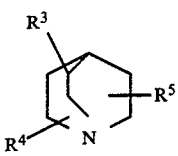

6. A compound according to claim 1 wherein R is

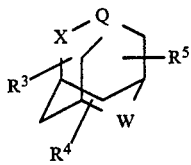

7. As a compound of claim 1, N-[2-[[[5-(dimethylamino)methyl-2-furanyl]methyl]thio]ethyl]-N'-[4-[2-(methoxy)ethoxy]benzyl]-2-nitor-1,1-ethenediamine.

8. As a compound of claim 1, N-cyano-N'-[2-[[[5(dimethylamino)methyl-2-furanyl]methyl]thio]ethyl]-N''-[2-[2-(methoxy)ethoxy]benzyl]guanidine.

9. As a compound of claim 1, N-[2-[[[5-(dimethylamino)methyl-2-furanyl]methyl]thio]ethyl]-N'''-[[[4-[2-(methoxy)ethoxy]benzyl]thio]propyl]-2-nitro-1,1-ethenediamine.

10. As a compound of claim 1, N-[2-[[[5-(dimethylamino)methyl-2-furanyl]methyl]thio]ethyl]-N'-[2-[[(7-methoxy-4-methylthio)cumaryl]ethyl]-2-nitro-1,1-ethenediamine.

11. As a compound of claim 1, N-[2-[[[5-(dimethylamino)methyl-2-furanyl]methyl]thio]ethyl]-N'-[2-(2-methylthioethyl)benzo-1,4-dioxan]-2-nitro-1,1-ethenediamine.

12. As a compound of claim 1, N-[2-[[[5-(dimethylamino)methyl-2-furanyl]methyl]thio]ethyl]-N'-[3(1-methoxy-indanyl-2-oxy)propyl]-2-nitro-1,1-ethenediamine.

13. As a compound of claim 1, N-[2-[[[5-(dimethylamino)methyl-2-furanyl]methyl]thio]ethyl]-N'-[2-[[2-[2,3-dihydrobenzofuranyl]methyl]thio]ethyl]-2-nitro-1,1-ethenediamine.

14. As a compound of claim 1, N-cyano-N'-[2-[[[5-(dimethylamino)methyl-2-furanyl]methyl]thio]ehtyl]-N''-[2-(5-methylbenzofuranyl)ethyl]-2-guanidine.

15. As a compound of claim 1, N-[2-[[[5-(dimethylamino)methyl-2-furanyl]methyl]thio]ethyl]-N'-[2-(1,4-benzodioxan-7-methylthio)ethyl]-2-nitro-1,1-ethenediamine.

16. As a compound of claim 1, N-cyano-N'-[2-[[[5-(dimethylamino)methyl-2-furanyl]methyl]thio]ethyl]-N''-[2-[1,4-benzodioxan-7-methyloxy]ethyl]guanidine.

17. As a compound of claim 1, N-[2-[[[5-(dimethylamino)methyl-2-furanyl]methyl]thio]ethyl]-N'''-[3-[2-(1,4-benzodioxan)]propyl]-2-nitro-1,1-ethenediamine.

18. As a compound of claim 1, N-cyano-N'-[2-[[[5-(dimethylamino)methyl-2-furanyl]methyl]thio]ethyl]-N''-[2-(1,3-benzodioxan-6-chloro-8-methylthio)ethyl]-guanidine.

19. As a compound of claim 1, N-[2-[[[5-(dimethylamino)methyl-2-furanyl]methyl]thio]ethyl]-N''-[2-(2,3-dihydrobenzofuranyl-2-methyl-5-methyloxy)]ethyl]-2-nitro-1,1-ethenediamine.

20. As a compound of claim 1, N-[2-[[[5-(dimethylamino)methyl-2-furanyl]methyl]thio]ethyl]-N'-[2-[3-(thionaphthenyl)methyleneoxy]ethyl]-2-nitro-1,1-ethenediamine.

21. As a compound of claim 1, N-[2-[[[5-(dimethylamino)methyl-2-furanyl]methyl]thio]ethyl]-N'-[2-[(6-methylcumarinyl)methyloxy]ethyl]-2-nitro-1,1-ethenediamine.

22. As a compound of claim 1, N-[2-[[[5-(dimethylamino)methyl-2-furanyl]methyl]thio]ethyl]-N'-[3-[(6-ethoxybenzothiazolyl)-2-thio]propyl]-2-nitro-1,1-ethenediamine.

23. As a compound of claim 1, N-cyano-N'-[2-[[[5-(dimethylamino)methyl-2-furanyl]methyl]thio]ethyl]-N''-[3,4-methylenedioxybenzyl]guanidine.

24. Pharmaceutical compositions having anti-ulcer, antisecretive and antihistaminic H2 activities, containing as the active principle at least one of compound according to claim 1, with suitable pharmaceutical diluents or carriers, optionally in association with other active principles.

25. Pharmaceutical compositions of claim 24, in form of capsules, tablets, dragees, syrups, solutions, sachets, vials for oral or parenteral administration.

* * * * *